US009687365B2

(12) United States Patent
Ásgeirsson et al.

(10) Patent No.: US 9,687,365 B2
(45) Date of Patent: *Jun. 27, 2017

(54) DORSI-PLANTAR PROSTHETIC ANKLE MODULE

(71) Applicant: Össur hf, Reykjavik (IS)

(72) Inventors: Sigurdur Ásgeirsson, Gardabaer (IS); David Landry, St-Jean-Chrysostôme (CA); Sigurdur Olafsson, Reykjavik (IS); Grímur Jónsson, Vogar (IS); Arinbjörn V. Clausen, Reykjavik (IS); Gudni Ingimarsson, Reykjavik (IS)

(73) Assignee: Össur hf, Reykjavik (IS)

( * ) Notice: Subject to any disclaimer, the term of this patent is extended or adjusted under 35 U.S.C. 154(b) by 0 days.

This patent is subject to a terminal disclaimer.

(21) Appl. No.: 14/830,102

(22) Filed: Aug. 19, 2015

(65) Prior Publication Data

US 2016/0051381 A1 Feb. 25, 2016

Related U.S. Application Data

(63) Continuation of application No. 13/622,991, filed on Sep. 19, 2012, now Pat. No. 9,114,029.
(Continued)

(51) Int. Cl.
*A61F 2/64* (2006.01)
*A61F 2/66* (2006.01)
(Continued)

(52) U.S. Cl.
CPC .............. *A61F 2/6607* (2013.01); *A61F 2/68* (2013.01); *A61F 2/66* (2013.01);
(Continued)

(58) Field of Classification Search
CPC ................................................. A61F 2002/745
See application file for complete search history.

(56) References Cited

U.S. PATENT DOCUMENTS 2,442,151 A * 5/1948 Strickland ............... A61F 2/602
623/49
4,306,320 A 12/1981 Delp
(Continued)

FOREIGN PATENT DOCUMENTS

WO WO 2011/035267 3/2011

*Primary Examiner* — Jacqueline Woznicki
(74) *Attorney, Agent, or Firm* — Knobbe, Martens, Olson & Bear, LLP

(57) ABSTRACT

An ankle module for a prosthetic foot can have an adapter portion pivotally coupled to a base portion. The base portion can be coupled to the prosthetic foot. The adapter portion can have a coupling member that removably couples the prosthetic foot to a prosthetic pylon or socket. The adapter portion can also have cylinders housing pistons slidably displaceable within the cylinders. An actuator is selectively actuatable to place the cylinders in fluid communication, allowing a fluid to flow between the cylinders as an angular position of the adapter portion is adjusted relative to the base portion, thereby adjusting the dorsi-plantar position between the adapter portion and the base portion of the ankle module. The actuator can be selectively actuatable to fluidly isolate the cylinders from each other so that the angular position of the adapter portion relative to the base portion remains substantially fixed.

20 Claims, 11 Drawing Sheets

Related U.S. Application Data

(60) Provisional application No. 61/536,990, filed on Sep. 20, 2011.

(51) Int. Cl.
  *A61F 2/68* (2006.01)
  *A61F 2/50* (2006.01)
  *A61F 2/74* (2006.01)
  *A61F 2/70* (2006.01)

(52) U.S. Cl.
  CPC .......... *A61F 2002/5003* (2013.01); *A61F 2002/5006* (2013.01); *A61F 2002/5018* (2013.01); *A61F 2002/5035* (2013.01); *A61F 2002/5073* (2013.01); *A61F 2002/6664* (2013.01); *A61F 2002/6854* (2013.01); *A61F 2002/6863* (2013.01); *A61F 2002/701* (2013.01); *A61F 2002/704* (2013.01); *A61F 2002/707* (2013.01); *A61F 2002/741* (2013.01); *A61F 2002/745* (2013.01); *A61F 2002/748* (2013.01)

(56) References Cited

U.S. PATENT DOCUMENTS

| | | |
|---|---|---|
| 4,413,360 A | 11/1983 | Lamb et al. |
| 5,139,525 A | 8/1992 | Kristinsson |
| 5,571,212 A | 11/1996 | Cornelius |
| 5,800,564 A | 9/1998 | Gelineau |
| 5,864,198 A | 1/1999 | Pinkerton |
| 5,888,212 A | 3/1999 | Petrofsky et al. |
| 5,888,239 A | 3/1999 | Wellershaus et al. |
| 5,913,901 A | 6/1999 | Lacroix |
| 5,944,760 A | 8/1999 | Christensen |
| 5,957,981 A | 9/1999 | Gramnäs |
| 6,187,052 B1 | 2/2001 | Molino et al. |
| 6,443,993 B1 | 9/2002 | Koniuk |
| 6,482,236 B2 | 11/2002 | Habecker |
| 6,602,295 B1 | 8/2003 | Doddroe et al. |
| 6,673,117 B1 | 1/2004 | Soss et al. |
| 6,855,170 B2 | 2/2005 | Gramnäs |
| 7,318,504 B2 | 1/2008 | Vitale et al. |
| 7,393,364 B2 | 7/2008 | Martin |
| 7,520,904 B2 | 4/2009 | Christensen |
| 7,637,957 B2 | 12/2009 | Ragnarsdottir et al. |
| 7,637,959 B2 | 12/2009 | Clausen et al. |
| 7,985,265 B2 | 7/2011 | Moser et al. |
| 8,206,458 B1 | 6/2012 | Hawkins |
| 9,114,029 B2 | 8/2015 | Ásgeirsson et al. |
| 2004/0044417 A1 | 3/2004 | Gramnas |
| 2005/0109563 A1 | 5/2005 | Vitale et al. |
| 2005/0137717 A1 | 6/2005 | Gramnäs et al. |
| 2007/0027557 A1 | 2/2007 | Jonsson et al. |
| 2007/0050045 A1 | 3/2007 | Clausen et al. |
| 2007/0050047 A1 | 3/2007 | Ragnarsdottlr et al. |
| 2007/0156252 A1 | 7/2007 | Jonsson et al. |
| 2008/0114470 A1 | 5/2008 | Hill et al. |
| 2008/0281435 A1 | 11/2008 | Abimosleh et al. |
| 2008/0300692 A1 | 12/2008 | Moser et al. |
| 2009/0204230 A1 | 8/2009 | Kaltenborn et al. |
| 2011/0160871 A1 | 6/2011 | Boone et al. |
| 2011/0307078 A1 | 12/2011 | Boender |

* cited by examiner

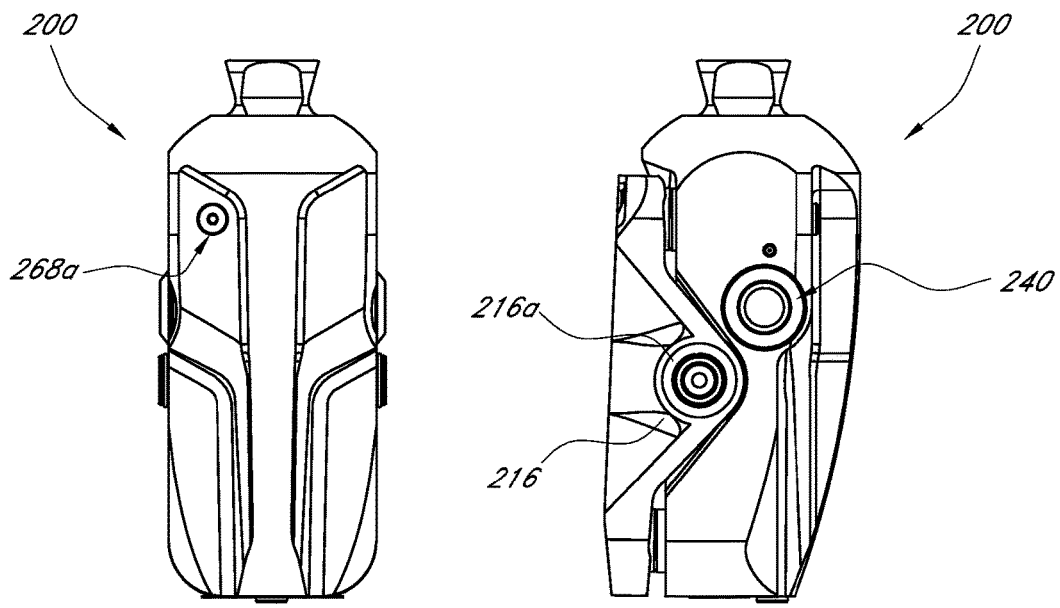
FIG. 3B  FIG. 3C
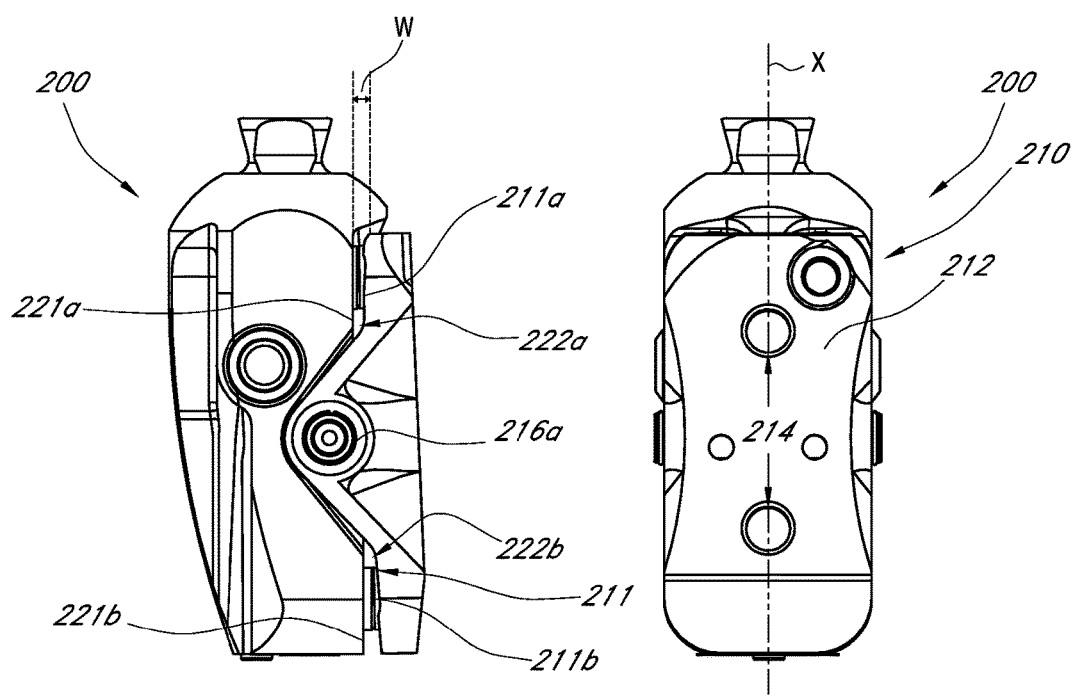
FIG. 3D  FIG. 3E

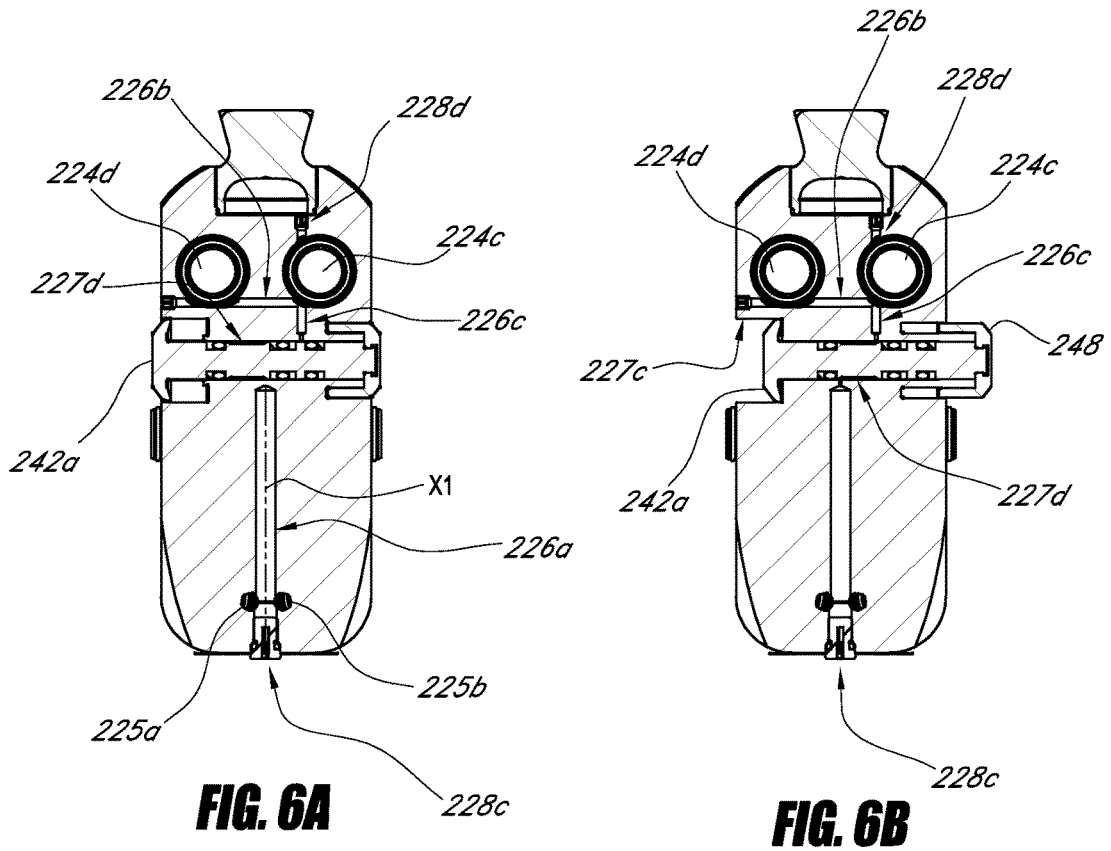
FIG. 6A  FIG. 6B
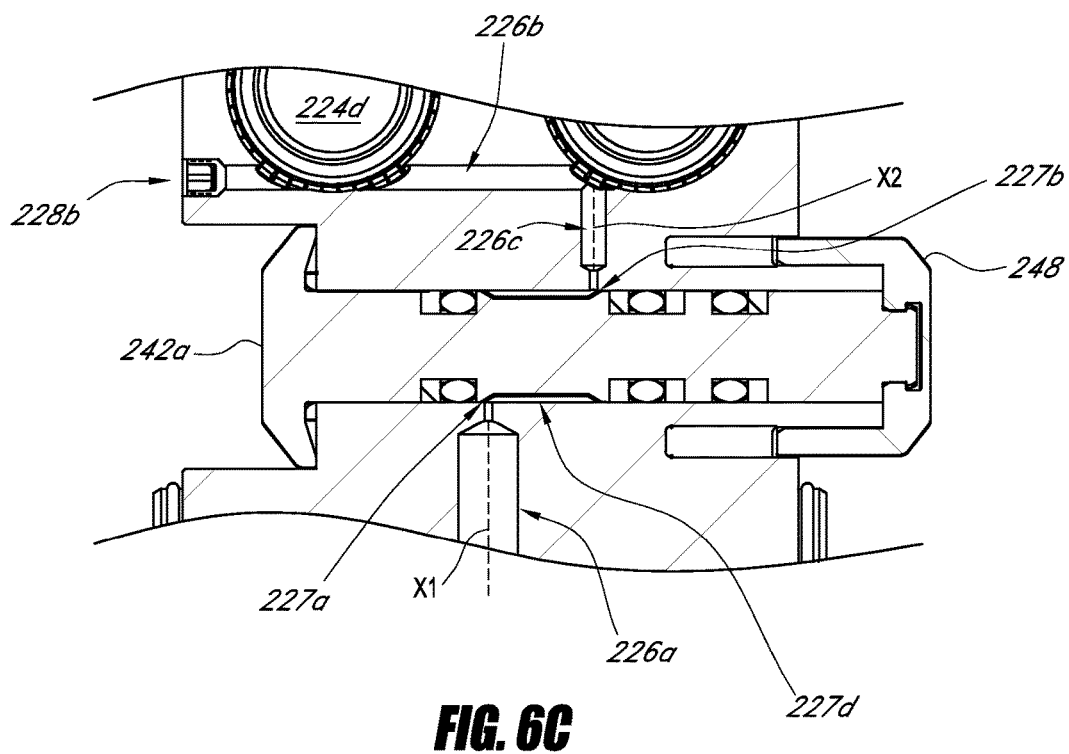
FIG. 6C

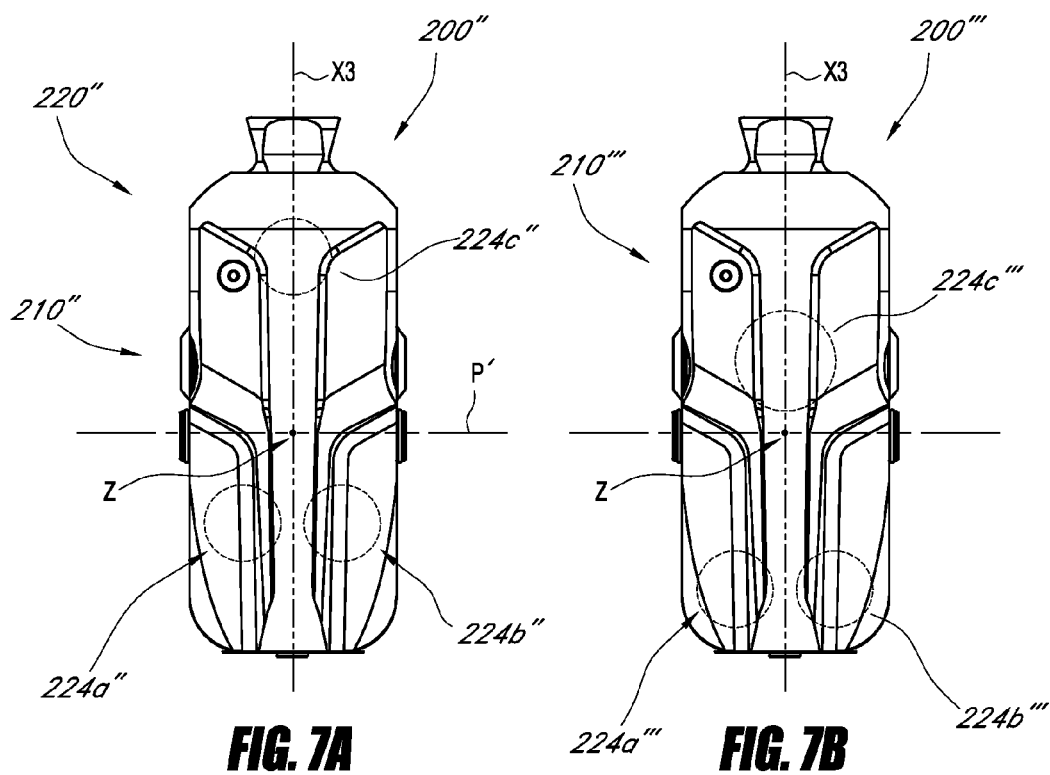

DORSI-PLANTAR PROSTHETIC ANKLE MODULE

CROSS-REFERENCE TO RELATED APPLICATION

This application is a continuation of U.S. application Ser. No. 13/622,991, filed Sep. 19, 2012, which claims the benefit of U.S. Provisional Application No. 61/536,990, filed Sep. 20, 2011, the entire contents of which are hereby incorporated by reference and should be considered a part of this specification.

BACKGROUND

Field

The present application relates in certain embodiments to prosthetic devices. In particular, the present application in certain embodiments relates to a dorsi-plantar adjustable ankle module for a prosthetic foot.

Description of the Related Art

Prosthetic feet of different designs are well known in the art. The various conventional designs have sought to solve various limitations associated with prosthetic feet.

Some prosthetic foot designs employ an ankle module pivotally or movably connected to the foot member to adjust the heel height of the prosthetic foot. However, such ankle modules tend to be bulky and/or complex.

Accordingly, there is a need for an improved ankle module that allows the adjustment of the relative angular position of a prosthetic foot with respect to a prosthetic shin component to adjust the heel height of the prosthetic foot, and that solves some of the problems discussed above.

SUMMARY

In accordance with one embodiment, a prosthetic foot is provided comprising a plate-like foot member extending from a proximal portion to a distal portion, the foot member curving downward and forward toward the distal portion. The prosthetic foot also comprises an ankle module removably coupleable to the proximal portion of the foot member. The ankle module comprises a base portion coupleable to the proximal portion so that a surface of the base portion contacts a surface of the proximal portion, and an adapter portion pivotally coupled to the base portion and having a coupling member configured to removably couple the foot member to a prosthetic pylon or socket. One of the base and adapter portions has three or more cylinders formed therein and aligned symmetrically relative to a pivot axis of the ankle module. The three or more cylinders house corresponding pistons slidably displaceable within the cylinders, the cylinders selectively placeable in fluid communication with each other. The ankle module further comprises an actuator selectively actuatable to place the three or more cylinders in fluid communication, allowing a hydraulic fluid to flow between the cylinders as an angular position of the adapter portion is adjusted relative to the base portion. The actuator is selectively actuatable to fluidly isolate the cylinders from each other so that the angular position of the adapter portion relative to the base portion remains substantially fixed, thereby adjusting the dorsi-plantar position between the adapter portion and the base portion of the ankle module.

In accordance with another embodiment, an ankle module removably coupleable to a prosthetic foot is provided. The ankle module comprises a base portion coupleable to a proximal portion of the prosthetic foot so that a planar surface of the base portion contacts a surface of the proximal portion of the prosthetic foot. The ankle module also comprises an adapter portion pivotally coupled to the base portion and having a coupling member configured to removably couple the prosthetic foot to a prosthetic pylon or socket. One of the base and adapter portions has three or more cylinders formed therein and aligned symmetrically relative to a pivot axis of the ankle module. The three or more cylinders house corresponding pistons slidably displaceable within the cylinders, the cylinders selectively placeable in fluid communication with each other. The ankle module further comprises an actuator selectively actuatable to place the three or more cylinders in fluid communication, allowing a hydraulic fluid to flow between the cylinders as an angular position of the adapter portion is adjusted relative to the base portion. The actuator is selectively actuatable to fluidly isolate the cylinders from each other so that the angular position of the adapter portion relative to the base portion remains substantially fixed, thereby adjusting the dorsi-plantar position between the adapter portion and the base portion of the ankle module.

In accordance with another embodiment, a prosthetic ankle module is provided, wherein the prosthetic ankle module is coupleable to a prosthetic foot member extending from a proximal portion to a distal portion. The ankle module comprises a base portion coupleable to the proximal portion of the foot member. The ankle module also comprises an adapter portion pivotally coupled to the base portion by a pivot. The ankle module further comprises a first piston assembly that comprises a first piston and a first cylinder, wherein the first piston is slidably displaceable within the first cylinder. The first piston assembly is coupled to the base portion and coupled to the adapter portion such that slidably displacing the first piston relative to the first cylinder causes the adapter portion to pivot relative to the base portion. The ankle module also comprises a second piston assembly that comprises a second piston and a second cylinder, wherein the second piston is slidably displaceable within the second cylinder. The second piston assembly is coupled to the base portion and coupled to the adapter portion such that slidably displacing the second piston relative to the second cylinder causes the adapter portion to pivot relative to the base portion. The first piston assembly and the second piston assembly may be selectively placeable in fluid communication with each other. The ankle module further comprises a valve that is fluidly coupled between the first piston assembly and the second piston assembly. An actuator may be coupled to the valve, wherein the actuator is actuatable to place the valve in a first position that places the first piston assembly in fluid communication with the second piston assembly and actuatable to place the valve in a second position that hydraulically seals the first piston assembly from the second piston assembly.

In accordance with another embodiment, a prosthetic foot comprises a foot member extending from a proximal portion to a distal portion, the foot member curving downward and forward toward the distal portion. The prosthetic foot also comprises an ankle module coupleable to the proximal portion of the foot member. The ankle module comprises a base portion coupleable to the proximal portion so that a surface of the base portion contacts a surface of the proximal portion. The ankle module further comprises an adapter portion coupled to the base portion. The ankle module also comprises an anterior linkage, wherein the anterior linkage is coupled to the base portion at a first point and the anterior linkage is coupled to the adapter portion at a second point.

An anterior axis goes through the first point and the second point. The ankle module further comprises a posterior linkage, wherein the posterior linkage is coupled to the base portion at a third point and the posterior linkage is coupled to the adapter portion at a fourth point. A posterior axis goes through the third point and the fourth point. The anterior linkage and the posterior linkage may be oriented relative to each other such that the anterior axis and the posterior axis intersect at a location that generally corresponds to an axis of rotation of a natural human ankle joint.

BRIEF DESCRIPTION OF THE DRAWINGS

FIG. 3B is a schematic front view of the dorsi-plantar ankle module in FIG. 1.

FIG. 3C is a schematic left side view of the dorsi-plantar ankle module in FIG. 1.

FIG. 3D is a schematic right side view of the dorsi-plantar ankle module in FIG. 1.

FIG. 3E is a schematic rear view of the dorsi-plantar ankle module in FIG. 1.

FIG. 6A is a schematic sagittal cross-sectional view of the dorsi-plantar ankle module in FIG. 1 in one operational configuration.

FIG. 6B is a schematic sagittal cross-sectional view of the dorsi-plantar ankle module in FIG. 1 in another operational configuration.

FIG. 6C is an enlarged sectional view of the dorsi-plantar ankle module in FIG. 6B.

FIG. 7A is a schematic view of another embodiment of a dorsi-plantar ankle module.

FIG. 7B is a schematic view of another embodiment of a dorsi-plantar ankle module.

DETAILED DESCRIPTION OF SOME EXEMPLIFYING EMBODIMENTS

Figure 1:
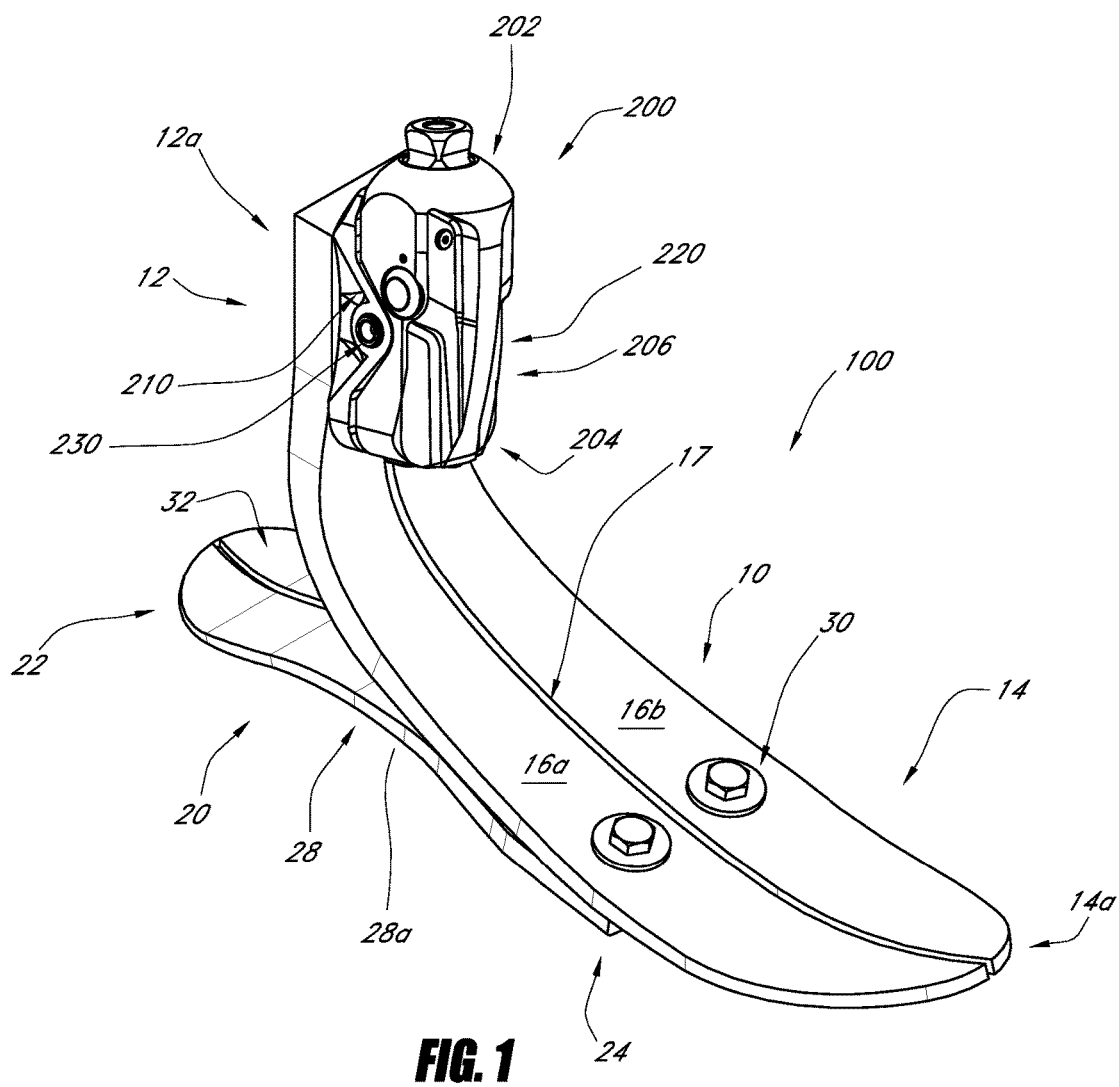
FIG. 1 is a schematic perspective view of one embodiment of a prosthetic foot coupled with one embodiment of a dorsi-plantar ankle module.

FIG. 1 shows one embodiment of a prosthetic foot 100 with a dorsi-plantar ankle module 200. The prosthetic foot 100 can have a foot member 10 that extends from a proximal section 12 to a distal section 14. In the illustrated embodiment, the proximal section 12 can be generally vertically oriented, and the distal section 14 can be generally horizontally oriented with the foot member 10 curving downward from the proximal section 12 to the distal section 14. The proximal section 12 can extend to a proximal end 12a and be generally at a location of a natural human ankle. In one embodiment, the distal section 14 can extend to a distal end 14a generally at a location of natural human toes.

With continued reference to FIG. 1, the foot member 10 can have multiple elongate segments that can flex independently relative to each other. In the illustrated embodiment, the foot member 10 has two elongate segments 16a, 16b that are separated from each other by a slot 17 that extends along a length between the distal end 14a and the proximal end 12a of the foot member 10. In one embodiment, the slot 17 extends along the entire length of the foot member 10. In another embodiment, the slot 17 extends along a length that is shorter than the entire length of the foot member 10. In one embodiment, the slot 17 extends linearly along its length, so that the width of all the elongate segments 16a, 16b is generally the same. In another embodiment, the slot 17 can have a curved section, such that one of the elongate segments has a different width than another of the elongate segments over at least a portion of their lengths.

The prosthetic foot 100 can also have a heel member 20 that extends between a proximal end 22 and a distal end 24 and is disposed below at least a portion of the foot member 10. In one embodiment, the heel member 20 can be coupled to the foot member 10 via one or more fasteners 30 (e.g., bolts) at a location between the proximal and distal ends 12a, 14a of the foot member 10 such that the heel member is cantilevered relative to the foot member 10 and extends to a free rear end at the proximal end 22. The heel member 20 can have a curvilinear profile along its length that defines an arch 28 between the proximal and distal ends 22, 24. The foot and heel members 10, 20 can define a slot 32 therebetween in the fore-aft direction at a rear portion of the prosthetic foot 100. In one embodiment, the slot 32 can taper toward a front end of the prosthetic foot 100. A resilient member (not shown) can be interposed between the heel member 20 and the foot member 10 within the slot 32. In one embodiment, the resilient member can separate at least a portion of the foot member 10 from the heel member 20. In another embodiment, the resilient member can completely separate the foot member 10 from the heel member 20.

In one embodiment, the foot and heel members 10, 20 are plate-like members with generally planar top and bottom surfaces and generally rectangular transverse cross-sections. The foot and heel members 10, 20 can be made of lightweight resilient materials, such as graphite, fiberglass, carbon fiber and the like. In some embodiments, the foot and heel members 10, 20 can be formed of multiple layers of material that define a monolithic piece.

With continued reference to FIG. 1, the prosthetic foot 100 can have an ankle module 200 that attaches to the proximal section 12 of the foot member 10. In the illustrated embodiment, the ankle module 200 extends generally vertically from a proximal end 202 to a distal end 204. The ankle module 200 can have a base 210 that couples (e.g., removably couples) to the proximal section 12 of the foot member 10. In one embodiment, the base 210 can couple to the foot member 10 via one or more fasteners (e.g., threaded fasteners), as further described below. In another embodiment, the base 210 can couple to the foot member 10 with an adhesive. In still another embodiment, the base can have a recess that receives at least a portion of the proximal portion 12 of the foot member 10 therein.

Figure 3A:
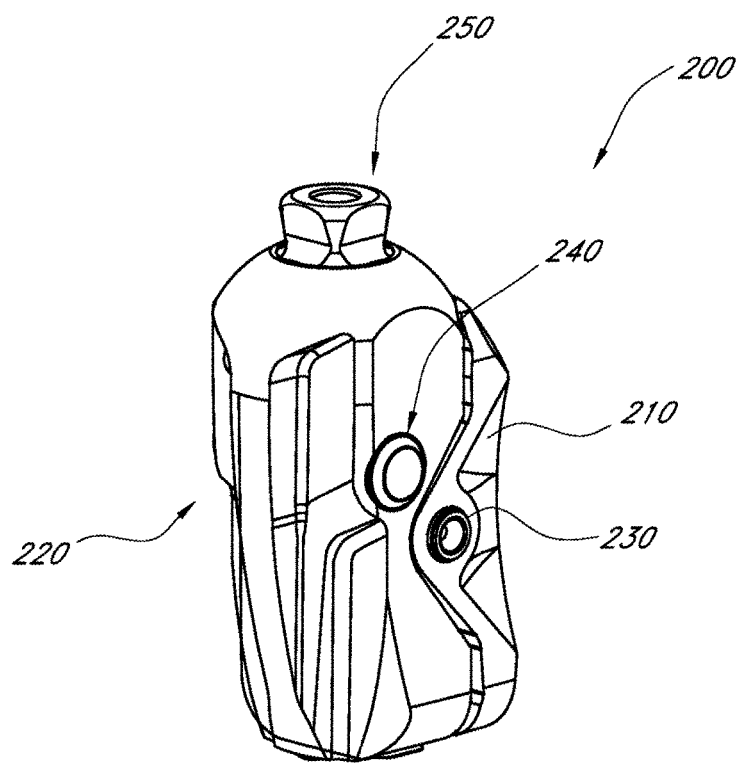
FIG. 3A is a schematic perspective view of the dorsi-plantar ankle module in FIG. 1.

The ankle module 200 can also have an adapter portion 220 that is pivotally coupled to the base 210. In the illustrated embodiment, the adapter portion 220 is pivotally coupled to the base 210 via an axle or pivot pin 230 located generally in a mid-portion 206 along the length of the ankle module 200. The adapter portion 220 can have a rear surface 221 (see FIG. 4A) that is spaced apart from a front surface 211 (see FIG. 4A, 4B) of the base 210 such that a gap 222a (see FIG. 3D) is defined above the pivot axis P between a proximal rear surface portion 221a of the adapter portion 220 and a proximal front surface portion 211a of the base 210, and a gap 222b is defined below the pivot axis between a distal rear surface portion 221b of the adapter portion 220 and a distal front surface portion 211b of the base 210. The width W of the gaps 222a, 222b can vary depending on the angular orientation of the adapter portion 220 relative to the base 210.

The ankle module 200 can also have an actuator 240 (see FIG. 3A) actuatable to selectively lock and unlock the angular orientation of the adapter portion 220 relative to the base 210. Advantageously, the orientation of the adapter portion 220 can be selectively adjusted by a user in the dorsi-plantar direction of the prosthetic foot 100. A connector 250 is disposed on the proximal end 202 of the adapter portion 220 for coupling the ankle module 200 to a prosthetic pylon or socket. In the illustrated embodiment, the connector 250 is a male pyramid connector. However, in other embodiments, the connector 250 can be a tube clamp. Further discussion of the features of the ankle module 200 is provided below.

Figure 2:
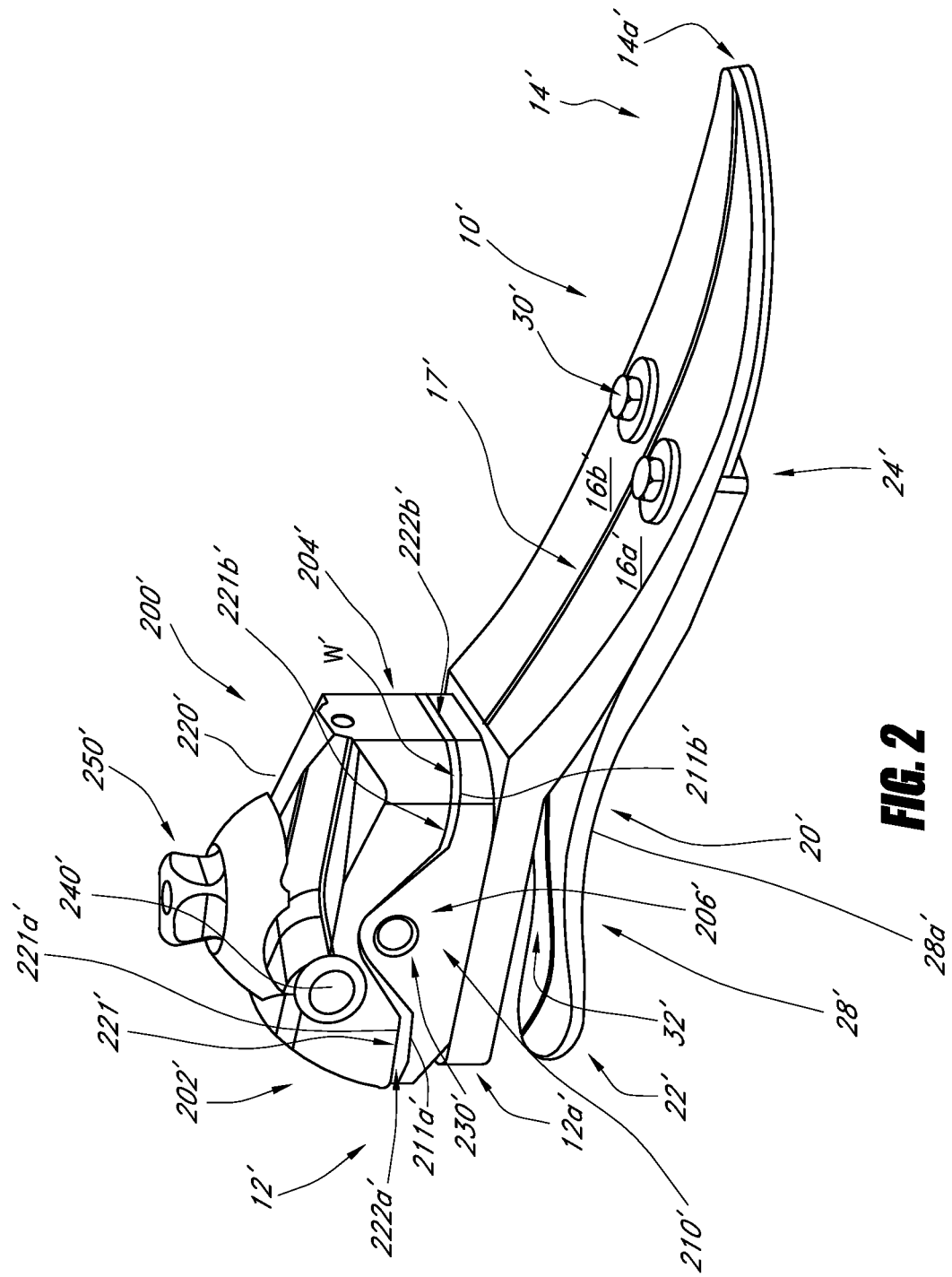
FIG. 2 is a schematic perspective view of another embodiment of a prosthetic foot coupled with another embodiment of a dorsi-plantar ankle module.

FIG. 2 shows another embodiment of a prosthetic foot 100' with a dorsi-plantar ankle module 200'. The prosthetic foot 100' and ankle module 200' are similar to the prosthetic foot 100 and ankle module 200 in FIG. 1, except as noted below. Thus, the reference numerals used to designate the various components of the prosthetic foot 100' and dorsi-plantar ankle module 200' are identical to those used for identifying the corresponding components of the prosthetic foot 100 and ankle module 200 in FIG. 1, except that a "'" has been added to the reference numerals.

The prosthetic foot 100' can have a foot member 10' that extends from a proximal section 12' to a distal section 14'. In the illustrated embodiment, the proximal section 12' can be generally horizontally oriented, and the distal section 14' can be generally horizontally oriented with the foot member 10 curving downward and forward from the proximal section 12' to the distal section 14'. The proximal section 12' can extend to a proximal end 12a' and be generally at a location of a natural human ankle. In one embodiment, the distal section 14' can extend to a distal end 14a' generally at a location of natural human toes.

The foot member 10' can have multiple elongate segments 16a', 16b' separated by a slot 17' such that the elongate members 16a', 16b' can flex independently relative to each other. As discussed above, the slot 17' can be straight or have a curved portion.

The prosthetic foot 100' can also have a heel member 20' that extends between a proximal end 22' and a distal end 24' and is disposed below at least a portion of the foot member 10'. In one embodiment, the heel member 20' can be coupled to the foot member 10' via one or more fasteners 30' (e.g., bolts) at a location between the proximal and distal ends 12a', 14a' of the foot member 10' such that the heel member 20' is cantilevered relative to the foot member 10' and extends to a free rear end at the proximal end 22'. The heel member 20' can have a curvilinear profile along its length that defines an arch 28' between the proximal and distal ends 22', 24'. The foot and heel members 10', 20' can define a slot 32' in the fore-aft direction at a rear portion of the prosthetic foot 100'. In one embodiment, the slot 32' can taper toward a front end of the prosthetic foot 100'. A resilient member (not shown) can be interposed between the heel member 20' and the foot member 10' within the slot 32'. In one embodiment, the resilient member can separate at least a portion of the foot member 10' from the heel member 20'. In another embodiment, the resilient member can completely separate the foot member 10' from the heel member 20'.

In one embodiment, the foot and heel members 10', 20' are plate-like members with generally planar top and bottom surfaces and generally rectangular transverse cross-sections. The foot and heel members 10', 20' can be made of lightweight resilient materials, such as graphite, fiberglass, carbon fiber and the like. In some embodiments, the foot and heel members 10', 20' can be formed of multiple layers of material that define a monolithic piece.

With continued reference to FIG. 2, the prosthetic foot 100' can have an ankle module 200' that attaches to the proximal section 12' of the foot member 10'. In the illustrated embodiment, the ankle module 200' extends generally horizontally from a proximal end 202' to a distal end 204'. The ankle module 200' can have a base 210' that couples (e.g., removably couples) to the proximal section 12' of the foot member 10'. In one embodiment, the base 210' can couple to the foot member 10' via one or more fasteners (e.g., threaded fasteners). In another embodiment, the base 210' can couple to the foot member 10' with an adhesive. In still another embodiment, the base can have a recess that receives at least a portion of the proximal portion 12' of the foot member 10' therein.

The ankle module 200' can also have an adapter portion 220' that is pivotally coupled to the base 210'. In the illustrated embodiment, the adapter portion 220' is pivotally coupled to the base 210' via an axle or pivot pin 230' located generally in a mid-portion 206' along the length of the ankle module 200'. The adapter portion 220' can have a rear surface 221' that is spaced apart from a front surface 211' of the base 210' such that a gap 222a' is defined proximally of the pivot axis P' between a proximal rear surface portion 221a' of the adapter portion 220' and a proximal front surface portion 211a' of the base 210', and a gap 222b' is defined distally of the pivot axis P' between a distal rear surface portion 221b' of the adapter portion 220' and a distal front surface portion 211b' of the base 210'. The width W' of the gaps 222a', 222b' can vary depending on the angular orientation of the adapter portion 220' relative to the base 210'.

The ankle module 200' can also have an actuator 240' actuatable to selectively lock and unlock the angular orientation of the adapter portion 220' relative to the base 210'. Advantageously, the orientation of the adapter portion 220' can be selectively adjusted by a user in the dorsi-plantar direction of the prosthetic foot 100'. A connector 250' is disposed on a top surface of the adapter portion 220' for coupling the ankle module 200' to a prosthetic pylon or socket, where the connector 250' is disposed between the proximal and distal ends 202', 204' of the ankle module 200'. In the illustrated embodiment, the connector 250' is a male pyramid connector. However, in other embodiments, the connector 250' can be a tube clamp.

In one embodiment, the prosthetic foot 100, 100' can be coupled (e.g., removably coupled) to a cosmesis foot cover (not shown) that has an upper portion and a sole portion. In one embodiment, the sole portion can have an insole with a convex surface that corresponds to the curvature of a concave bottom surface 28a, 28a' of the arch 28, 28' of the heel member 20, 20', such that the insole maintains contact with the bottom surface 28a, 28a' of the heel member 20, 20' during ambulation of the prosthetic foot 100, 100' from heel strike to toe-off.

Further details on prosthetic feet can be found in U.S. Publication No. 2005/0038524; U.S. Pat. No. 7,846,213; U.S. application Ser. No. 13/034,474, filed Feb. 24, 2011, and titled "Prosthetic Foot with a Curved Split," and U.S. application Ser. No. 13/149,118, filed May 31, 2011, and titled "Height-adjustable Threaded Shock Absorbing Module and Associated Coupling Member," the entire contents of all of which are hereby incorporated by reference and should be considered a part of this specification. Further details of foot covers and insole portions can be found in U.S. Publication No. 2010/0004757 titled "Smooth Rollover Insole for Prosthetic Foot" and U.S. Publication No. 2006/0015192 titled "Functional Foot Cover," the entire contents of all of which are hereby incorporated by reference and should be considered a part of this specification.

FIGS. 3-6B further illustrate the dorsi-plantar ankle module 200 shown in FIG. 1. One or more apertures 214 extend through the base 210 from the front surface 211 to a rear surface 212 of the base 210. In the illustrated embodiment, the base 210 has two apertures 214 aligned along a longitudinal axis X of the base 210. The apertures 214 can be sized to receive fasteners therethrough, such as threaded fasteners (e.g., bolts), to fasten the base 210 to the proximal section 12 of the foot member 10. The base 210 can also have a pair of raised side walls 216 on the medial and lateral sides of the base 210, where the side walls 216 have apertures 216a therein sized to receive the axle 230 of the ankle module 200 therethrough, the apertures 216a aligned so as to define the pivot axis P when the adapter portion 220 is coupled to the base 210. As best shown in FIG. 3C, the side walls 216 can be v-shaped.

The front surface 211 of the base 210 can have three or more recesses 218 formed therein. In the illustrated embodiment, the front surface 211 has four recesses 218a-d arranged symmetrically along the longitudinal axis X of the base 210 and about the pivot axis P. In one embodiment, the recesses 218a-d are cylindrical and have the same diameter. In another embodiment, one or more of the recesses 218a-d can have a different diameter. In one embodiment, the recesses 218a-d extend partially through the base 210. In another embodiment, one or more of the recesses 218a-d extends completely through the base 210. In the illustrated embodiment, one of the recesses 218a extends completely through the base 210, and the rest of the recesses 218b-d extend partially through the base 210. The front surface 211 can also have a recessed portion 219 between the side walls 216. In the illustrated embodiment, the recessed portion 219 is generally square shaped.

The adapter portion 220 can have three or more cylinders 224 formed therein. In the illustrated embodiment, the adapter portion 220 has four cylinders 224a-d disposed symmetrically relative to the pivot axis P, with two distal cylinders 224a, 224b disposed below the pivot axis P and two proximal cylinders 224c, 224d disposed above the pivot axis P. In the illustrated embodiment, the cylinders 224a-d have the same cylindrical shape and diameter. In another embodiment, one or more of the cylinders 224a-d can have a different shape or diameter. The two distal cylinders 224a, 224b each have an aperture 225a, 225b formed therein that communicate with a first passage 226a so that the distal cylinders 224a, 224b are in fluid communication with each other. The two proximal cylinders 224c, 224d have an aperture 225c, 225d formed therein that interconnect the cylinders 224c, 224d via a second passage 226b, so that the proximal cylinders 224c, 224d are in fluid communication with each other. In the illustrated embodiment, the first passage 226a extends through the adapter portion 220 to an aperture 227a in a valve chamber 227 along a lengthwise axis X1 of the adapter portion 220. The valve chamber 227 can extend generally transversely (e.g., horizontally) to the longitudinal axis of the adapter portion 220. A third passage 226c extends from the proximal cylinder 224c to an aperture 227b in the valve chamber 227 generally along a lengthwise axis X2 that is offset from the lengthwise axis X1.

With continued reference to FIGS. 3-6B, the rear of the adapter portion 220 can include an intermediate portion 221c that is raised relative to the proximal and distal rear surface portions 221a, 221b. A passage 228 is defined in the intermediate portion 221c and extends transversely relative to the longitudinal axis of the adapter portion 220. The passage 228 can be sized to receive the axle or pivot pin 230 therethrough. The medial and lateral sides of the adapter portion 220 can have recessed side portions 221d about the passage 228. In the illustrated embodiment, the recessed side portions 221d can be v-shaped and correspond to the shape of the side walls 216 of the base 210. Advantageously, the side walls 216 can fit within the recessed side portion 221d so that the apertures 216a of the side walls 216 align with the passage 228, allowing the axle 230 to pass through the apertures 216a and the passage 228, so that the assembled ankle module 200 has a reduced profile in the anterior-posterior direction. Additionally, the raised intermediate portion 221c can fit within the recessed portion 219 of the base 210 that is between the side walls 216.

Figure 4A:
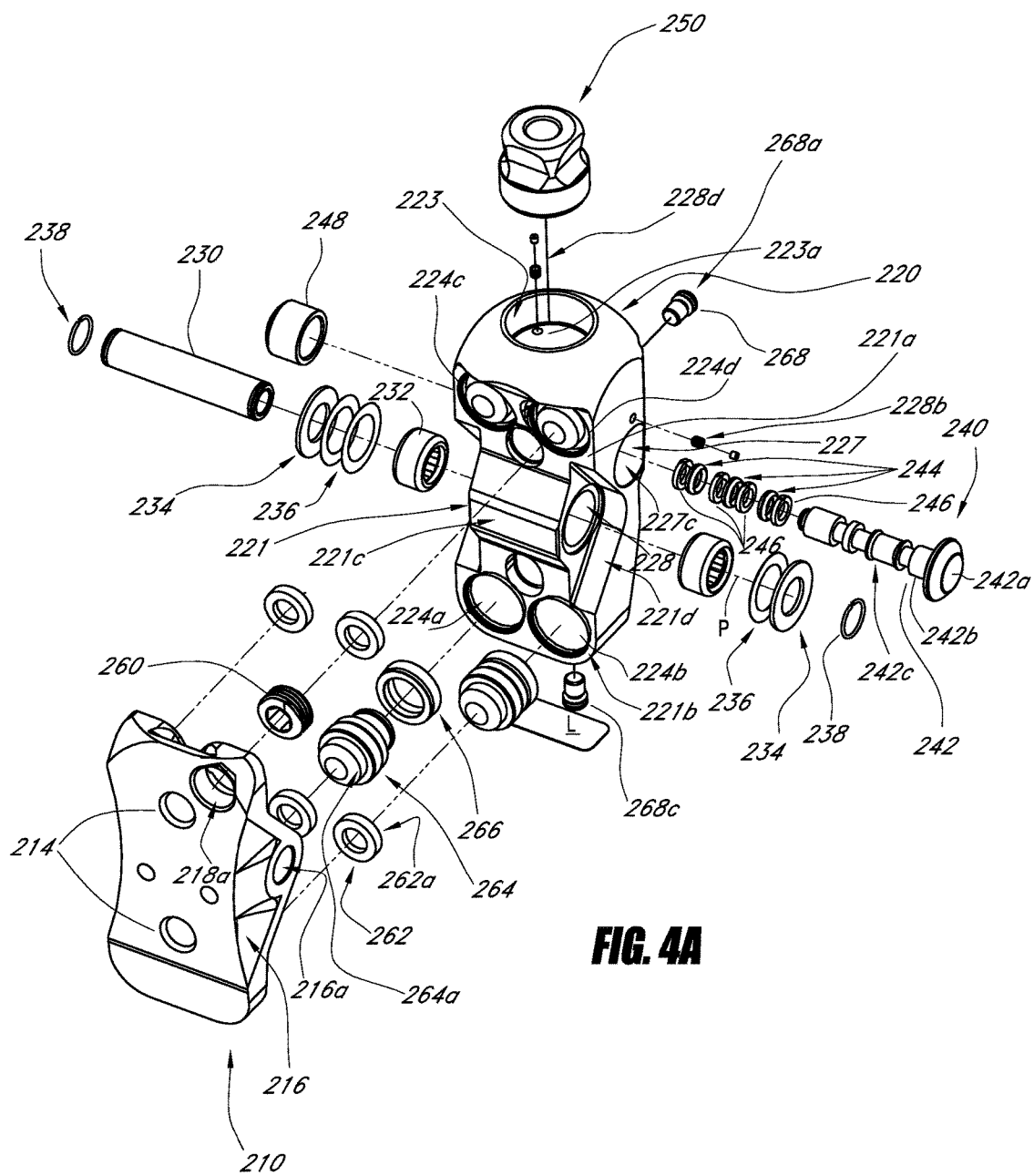
FIG. 4A is a schematic exploded view of the dorsi-plantar ankle module in FIG. 1.
Figures 4B, 4C:
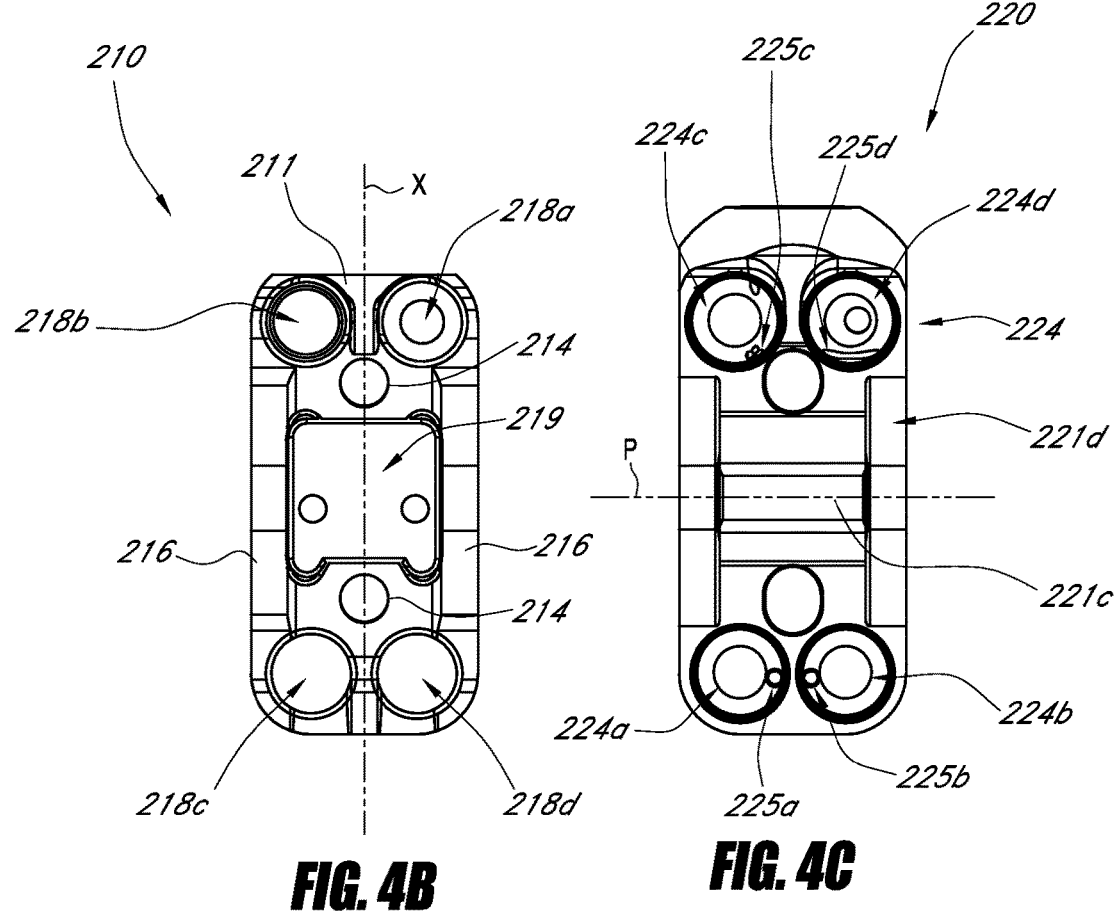
FIG. 4B is a schematic front view of a base of the dorsi-plantar module in FIG. 1.
FIG. 4C is a schematic rear view of an adapter portion of the dorsi-plantar module in FIG. 1.

As best shown in FIG. 4A, two roller bearings 232 can be disposed on opposite sides of the pivot pin 230 and within the passage 228. Additionally, one or more washers 234 and one or more shims 236 can be disposed on opposite sides of the pivot pin 230 and within the recessed side portion 221d between the side walls 216 of the base 210 and the side of the adapter portion 220. Snap rings 238 can be disposed on both ends of the pivot pin 230 that protrude from the side walls 216 of the base 210, so that the rings 238 inhibit the lateral movement of the pivot pin 230.

The actuator 240 can include a spool valve 242 that movably extends through the valve chamber 227. The spool valve 242 can have a push button 242a on one end that can travel within a side chamber 227c in a side of the adapter portion 220 as a shaft 242b of the spool valve 242 travels within the valve chamber 227. The spool valve 242 can also have a reduced diameter portion 242c that defines a gap (e.g., radial gap) 227d between the spool valve 242 and a surface of the valve chamber 227. The reduced diameter portion 242c can have a length that allows the spool valve 242 to be selectively positioned within the valve chamber 227 so that the apertures 227a, 227b fluidly communicate with each other via the gap 227d, as further described below. The spool valve 242 can also have one or more seals (e.g., o-rings) 244 and one or more back-up rings 246 (e.g., split back-up rings) disposed on the shaft 242b on either side of the reduced diameter portion 242c to substantially seal the reduced diameter portion 242c within the valve chamber 227. A cover 248 can be disposed on an end of the spool valve 242 opposite the push button 242a.

With continued reference to FIG. 4A, the ankle module 200 can include a set screw 260 insertable into the recess 218a. The set crew 260 can be adjusted to adjust the depth of the recess 218a. In one embodiment, the set screw 260 is adjusted so that the depth of the recesses 218a-d is generally equal. Each of the recesses 218a-d can be sized to removably receive a spherical washer 262 therein, which can have a spherical anterior surface 262a (see FIG. 5) that contacts a corresponding end surface 264a a piston 264 that is slidably disposed in one of the cylinders 224a-d. In the illustrated embodiment, the ankle module 200 has four washers 262 that interface with four pistons 264, respectively. A seal 266 can be disposed on an opposite end 264b of each piston 264, so that the seal 266 is radially interposed between at least a portion of the piston 264 and the corresponding cylinder 224a-d wall to thereby fluidly seal the cylinder 224a-d. The ankle module 200 can also include one or more plugs 268 that fluidly seal passages within the adapter portion 220. In the illustrated embodiment, the ankle module 200 has a first plug 268a that seals an aperture in one of the cylinders 224d, a second plug 228b that seals the second passage 226b between the cylinders 224c, d, a third plug 228c that seals the first passage 226a, and a fourth plug 228d that seals an aperture 223a in a recess opening 223 that receives the connector 250. The ankle module 200 can have a label L with information (e.g., serial number) of the module.

A hydraulic fluid is disposed in the cylinders 224a-d between the proximal ends 264b of the pistons 264 and the base of the cylinders 224a-d. The hydraulic fluid is also disposed in the passages 226a-c and the gap 227d between the spool valve 242 and a surface of the valve chamber 227.

In operation, the spool valve 242 can be actuated to slide the shaft 242b within the valve chamber 227 so that the gap 227d communicates with the apertures 227a, b. For example, a user can push on the push button 242a to slide the spool valve 242 within the valve chamber 227. This allows the proximal cylinders 224c, d to be in fluid communication with the distal cylinders 224a, b. The angular orientation of the adapter portion 220 can then be adjusted relative to the base 210 by pivoting the adapter portion 220 relative to the base 210 about the pivot axis P, thereby causing hydraulic fluid to transfer between the proximal cylinders 224c, d and the distal cylinders 224a, b. Once the desired angular orientation of the adapter portion 220 is obtained, the spool valve 242 can be actuated to slide the shaft 242b so that the gap 227d does not communicate with both of the apertures 227a, b, thereby fluidly isolating the proximal cylinders 224c, d from the distal cylinders 224a, b and substantially locking the angular position of the adapter portion 220 relative to the base 210. For example, the user can push on the cover 248 on the opposite side of the shaft 242b from the push button 242a.

Figure 5:
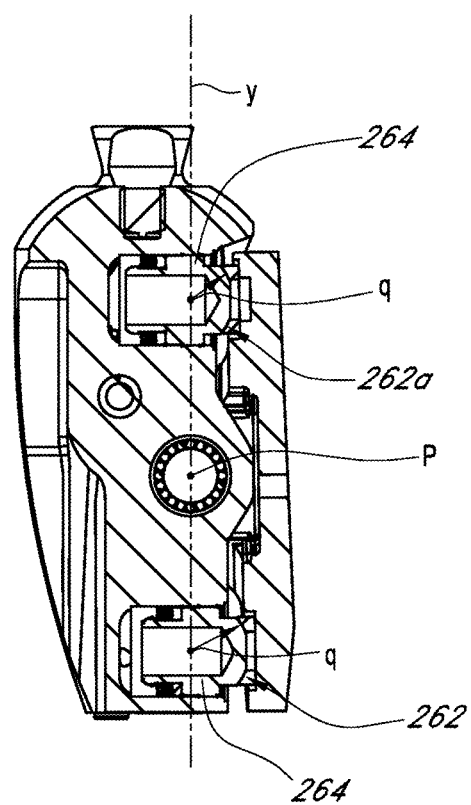
FIG. 5 is a schematic longitudinal cross-sectional view of the dorsi-plantar ankle module in FIG. 1.

Advantageously, since the proximal cylinders 224c, d are in fluid communication with each other via the second passage 226b and the distal cylinders 224a, b are in fluid communication with each other via the first passage 226a, the hydraulic pressure in the proximal cylinders 224c, d is substantially equal, and the hydraulic pressure in the distal cylinders 224a, b is substantially equal, so that a balance in pressure is achieved in the proximal cylinders 224c, d and the distal cylinders 224a, b. Additionally, the diameter, shape and number of cylinders 224a-d and pistons 264, as well as their placement relative to the pivot axis P is advantageously such that the volume of hydraulic fluid that is displaced as the angular orientation of the adapter portion 220 is adjusted remains balanced (e.g., the cross-sectional area of the proximal cylinders 224c, d times the distance the cylinders 224c, d are spaced from the pivot axis P is equal to the cross-sectional area of the distal cylinders 224a, b times the distance the cylinders 224 a, b are spaced from the pivot axis P). For example, as shown in FIG. 5, the cylinders 224a-d are located in the adapter portion 220 such that a plane Y crosses through the pivot axis P, the pistons 264 and the conical center of rotation "q" of the spherical surface 262a of the spherical washers 262, which advantageously ensures the displaced volume of hydraulic fluid is balanced between the cylinders 224a-d. In contrast, if the displaced volume of hydraulic fluid is unbalanced (e.g., the area of the proximal cylinders 224c, d times the distance the cylinders 224 c, d are spaced from the pivot axis P does not equal the area of the distal cylinders 224a, b times the distance the cylinders 224 a, b are spaced from the pivot axis P), this can result in the creation of a void in the hydraulic passage or lead to compressing an incompressible fluid, thereby causing the ankle module to either be loose or not move, respectively, when the user looks to rotate the adapter module 220 relative to the base 210. In one embodiment, an accumulator (e.g., a bladder, compressible element) (not shown) can be included in the hydraulic fluid system to compensate for minor errors (or usage of a double acting cylinder) in the diameters of the cylinders 224a-d or their placement from the pivot axis P.

FIG. 7A shows another embodiment of an ankle module 200". The ankle module 200" is similar to the ankle module 200 in FIG. 1, except as noted below. Thus, the reference numerals used to designate the various components of the dorsi-plantar ankle module 200" are identical to those used for identifying the corresponding components of the ankle module 200 in FIG. 1, except that a """ has been added to the reference numerals.

In the illustrated embodiment, the ankle module 200" has three cylinders 224a"-c", with two distal cylinders 224a", b" and a single proximal cylinder 224c". The cylinders 224a"-c" have the same diameter and shape, but are located relative to the pivot location P', so that the volume of hydraulic fluid that is displaced between the cylinders 224a"-c" as the angular orientation of the adapter portion 220" is adjusted remains balanced.

FIG. 7B shows another embodiment of an ankle module 200". The ankle module 200'" is similar to the ankle module 200 in FIG. 1, except as noted below. Thus, the reference numerals used to designate the various components of the dorsi-plantar ankle module 200'" are identical to those used for identifying the corresponding components of the ankle module 200 in FIG. 1, except that a """ has been added to the reference numerals.

The ankle module 200'" has three cylinders 224a'"-c'", with two distal cylinders 224a'", b'" and a single proximal cylinder 224c'". In the illustrated embodiment, the diameter of the proximal cylinder 224c'" is larger than the diameter of the distal cylinders 224a'", b'", so the location of the cylinders 224a'"-c'" relative to the pivot location P' is different than in the ankle module 200" so that the volume of hydraulic fluid that is displaced between the cylinders 224a'"-c'" as the angular orientation of the adapter portion 220'" is adjusted remains balanced. As shown in FIG. 7B, the proximal cylinder 224c'" is located closer to the pivot location P' than the proximal cylinder 224c" in FIG. 7A. Similarly, the distal cylinders 224a'", b'" are located farther from the pivot location P' than the distal cylinders 224a'", b'".

With continued reference to FIGS. 7A-B, in the illustrated embodiments, the pivot location P' is a pivot axis about which the adapter portion 220", 220'" of the ankle module 200", 200'" pivots relative to the base 210", 210'" via an axle or pivot pin in a similar manner as described above for the ankle module 200 shown in FIGS. 3A-6B. In another embodiment, the adapter portion 220", 220'" can be pivotally coupled to the base 210", 210'" via a single pivot point or point connection (e.g., a spherical bearing), allowing the adapter portion 220", 220'" to provide a spherical degree of freedom to the ankle module 200", 200'" where the adapter portion 220", 220'" can pivot about the longitudinal axis X3

(medial-laterally) and about the normal axis Z, in addition to pivoting in a dorsi-plantar manner about the transverse axis P.

Figure 8:
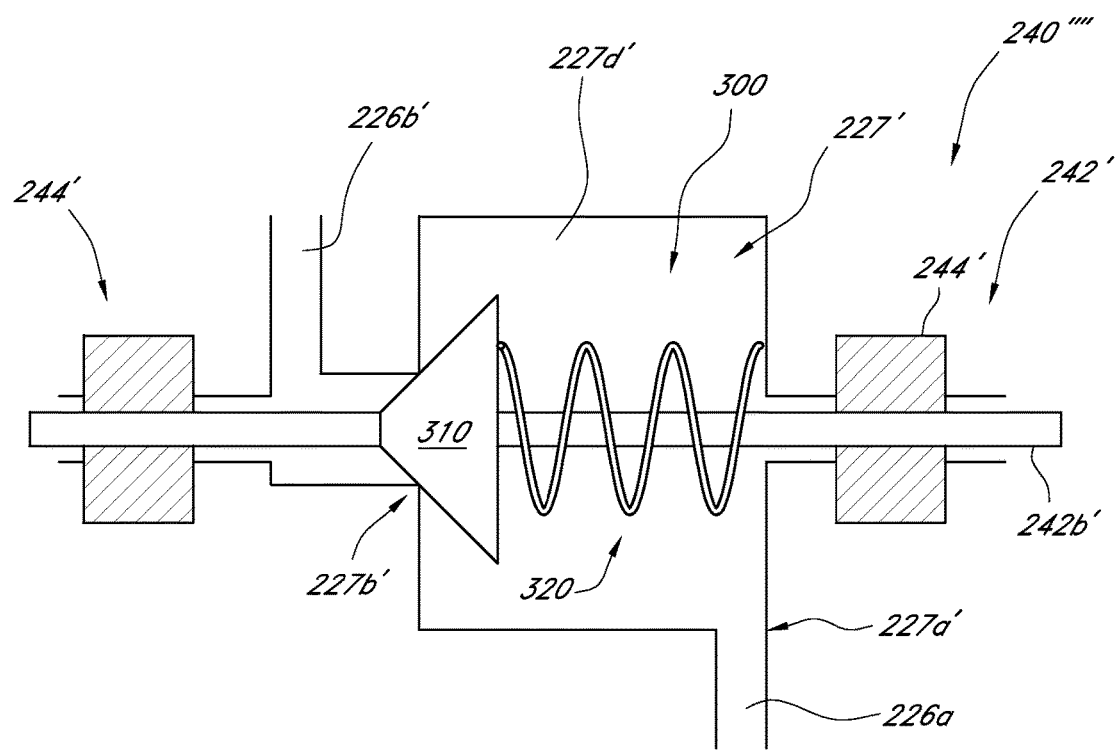
FIG. 8 is a schematic view of a relief valve for use with a dorsi-plantar ankle module.

FIG. 8 shows a schematic view of an actuator 240'''' that includes a relief valve 300 combined with a spool valve 242' similar to the spool valve 242 discussed above. In the illustrated embodiment, the relieve valve 300 includes a seal member 310, which is disposed about a shaft 242b' of the actuator 240', and a spring 320 that biases the seal member against an aperture 227b' in the valve chamber 227' that communicates with a second passage 226b' on the high pressure side of the ankle module 200, 200'', 200'''. One or more seals 244' substantially seal the actuator 240' relative to the environment outside the valve chamber 227'. In operation, the actuator 240' could be actuated, as discussed above, to place the passages 226a', 226b', and the cylinders they communicate with, in fluid communication with each other, allowing the angular orientation of the adapter portion 220, 220'', 220''' to be adjusted relative to the base 210, 210'', 210'''. In this position, the seal member 310 would not abut against the aperture 227b' in the valve chamber 227'. When the actuator 240' is actuated to isolate the passages 226a', 226b', and the cylinders they communicate with, from each other, the seal member 310 can abut against the aperture 227b', and be maintained in such a position by the biasing force of the spring 320, thereby substantially sealing the second passage 226b' relative to the valve chamber 227', thereby substantially locking the orientation of the adapter portion 220, 220'', 220''' relative to the base 210, 210'', 210'''. However, where the load placed on the ankle module 200, 200'', 200''' is of such a magnitude that the hydraulic pressure in the second passage 226b' provides a force on the seal member 310 that is greater than the bias force of the spring 320, the seal member 310 can be displaced away from the aperture 227b', allowing the pressure in the second passage 226b' to equalize with the pressure in the valve chamber 227' and/or first passage 226a' so that the seal member 310 can against be biased against the aperture 227b' to seal the aperture 227b'. Advantageously, use of the relief valve 300 allows the ankle module 200, 200'', 200''' to adjust when subjected to excessive loads or shocks, and to substantially inhibit leakage of hydraulic fluid from the adapter portion 220, 220'', 220''' to the environment as a result of said excessive load or shock. Additionally, the relief valve 300 can advantageously allow the ankle module 200, 200'', 200''' to behave (e.g., bend) in a similar manner as a sound human ankle.

In the embodiments described above, the actuator 240, 240' is a mechanical actuator that can be manually actuated by a user to selectively adjust or lock the angular orientation of the adapter portion 220, 220'', 220''' relative to the base 210, 210'', 210'''. In some embodiments, the actuator 240, 240' can include a mechanism to reduce the force required to actuate the spool valve 242, such as a lever mechanism, a threaded mechanism or an inclined plane mechanism. In another embodiment, the actuator can be a latch type actuator that has a preloaded spring mounted valve, where the user can actuate the latch to move the valve. In still other embodiments, the actuator 240, 240' can be a powered actuator, such as electro-mechanical actuator (e.g., a rotational actuator to turn a threaded mechanism, linear actuator based on a power screw, etc.), a computer processor controlled actuator, and a magnetic actuator (e.g., solenoid actuator). In other embodiments, the actuator 240, 240' can be remotely actuated by the user using a lanyard remote or a wireless remote that communicates wirelessly (e.g., via Rf signals) with the actuator 240, 240'. In another embodiment, the actuator can be a valve actuator that can include a valve that is operated by a solenoid, which can be remotely actuated by a user (e.g., wirelessly via a remote control).

Figure 9:
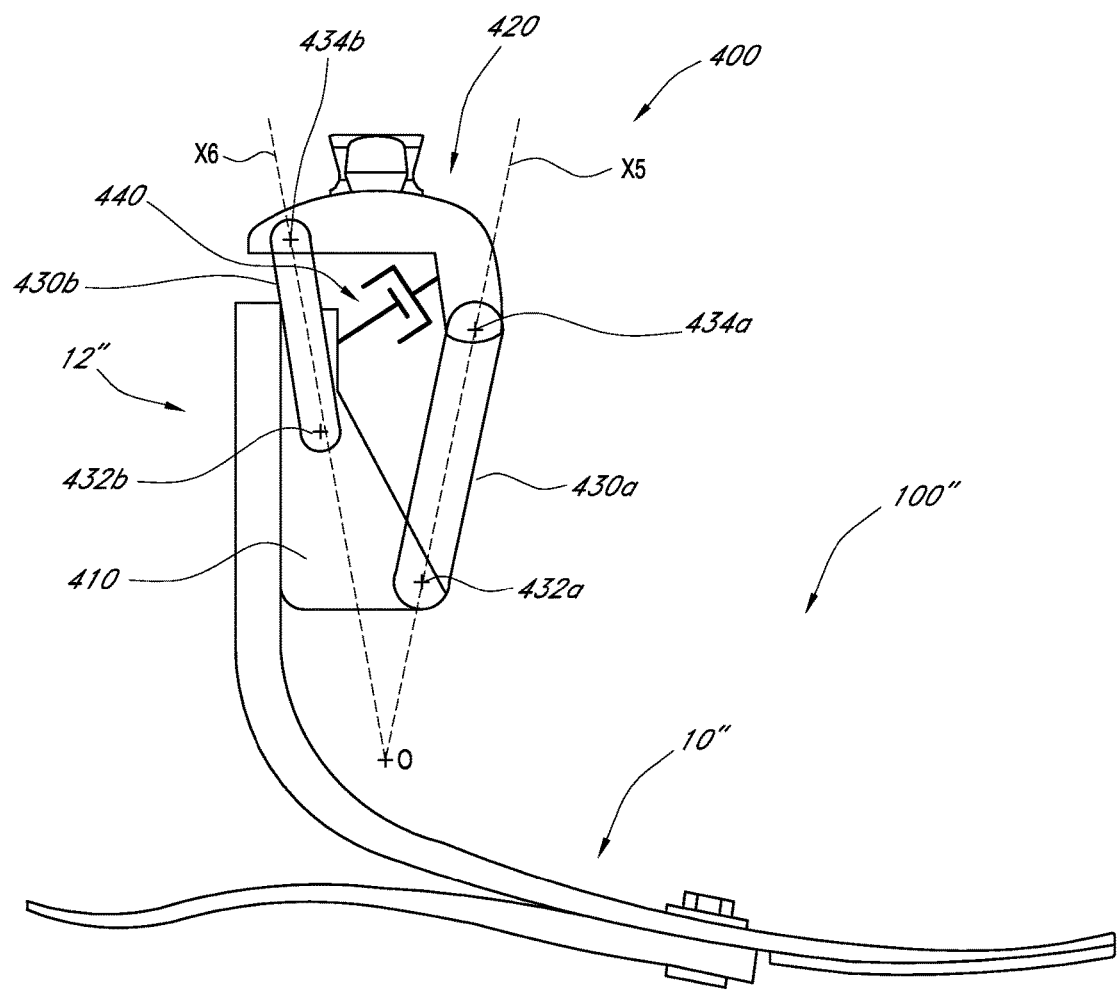
FIG. 9 is a schematic side view of another embodiment of a dorsi-plantar ankle module coupled to a prosthetic foot.

FIG. 9 shows another embodiment of a dorsi-plantar ankle module 400 for a prosthetic foot 100''. The prosthetic foot 100'' is similar to the prosthetic foot 100 in FIG. 1, except as noted below. Thus, the reference numerals used to designate the various components of the prosthetic foot 100'' are identical to those used for identifying the corresponding components of the prosthetic foot 100 in FIG. 1, except that a "''''" has been added to the reference numerals.

In the illustrated embodiment, the ankle module 400 can have a base portion 410 that couples to a proximal portion 12'' of the foot member 10'' of the prosthetic foot 100''. The ankle module 400 can also have an adapter portion 420 movably coupled to the base portion 410 via one or more levers or linkages. In the illustrated embodiment, the adapter portion 420 is movably coupled to the base 410 via an anterior lever 430a and a posterior lever 430b, both of which interconnect the adapter portion 420 and the base 410, where the levers 430a, 430b can pivot about pivot points 432a, 432b on the base 410 and pivot points 434a, 434b on the adapter portion 420. The ankle module 400 can also have a damper 440 between the adapter portion 420 and base 410 that limits the degree and speed of angular rotation of the adapter portion 420 relative to the base 410. With continued reference to FIG. 9, the anterior and posterior levers 430a, 430b can extend at an angle relative to each other such that their respective axes X5, X6 intersect at a point O generally corresponding to an axis of rotation of a natural human ankle joint, which advantageously allows the displacement of the toe and heel portions of the foot 100'' to approximate that of a sound human foot when pivoting the foot 100'' via the ankle module 400.

Of course, the foregoing description is that of certain features, aspects and advantages of the present invention, to which various changes and modifications can be made without departing from the spirit and scope of the present invention. Moreover, the ankle module need not feature all of the objects, advantages, features and aspects discussed above. Thus, for example, those skill in the art will recognize that the invention can be embodied or carried out in a manner that achieves or optimizes one advantage or a group of advantages as taught herein without necessarily achieving other objects or advantages as may be taught or suggested herein. In addition, while a number of variations of the invention have been shown and described in detail, other modifications and methods of use, which are within the scope of this invention, will be readily apparent to those of skill in the art based upon this disclosure. It is contemplated that various combinations or subcombinations of the specific features and aspects between and among the different embodiments may be made and still fall within the scope of the invention. Accordingly, it should be understood that various features and aspects of the disclosed embodiments can be combined with or substituted for one another in order to form varying modes of the discussed dorsi-plantar ankle module.

What is claimed is:

1. An ankle module removably coupleable to a proximal portion of a prosthetic foot comprising:
   a base portion coupleable to the proximal portion so that a planar surface of the base portion contacts a surface of the proximal portion of the prosthetic foot, wherein the base portion comprises a central vertical axis and a length extending along the central vertical axis;

an adapter portion pivotally coupled to the base portion at a pivot connection located generally at a mid-point along the length of the ankle module and having a coupling member configured to removably couple the prosthetic foot to a prosthetic pylon or socket, one of the base and adapter portions having three or more cylinders formed therein, the three or more cylinders being aligned symmetrically relative to the pivot connection of the ankle module, the three or more cylinders housing corresponding pistons slidably displaceable within the cylinders, the cylinders selectively placeable in fluid communication with each other, wherein the adapter portion is pivotally coupled to the base portion about the pivot connection such that the adapter portion is allowed to pivot medial-laterally about a longitudinal axis, in a dorsi-plantar manner about a transverse axis, and about a normal axis relative to the base portion; and an actuator selectively actuatable to place the three or more cylinders in fluid communication, allowing a hydraulic fluid to flow between the cylinders as an angular position of the adapter portion is adjusted relative to the base portion, the actuator selectively actuatable to fluidly isolate the cylinders from each other so that the angular position of the adapter portion relative to the base portion remains fixed, thereby adjusting the dorsi-plantar position between the adapter portion and the base portion of the ankle module.

2. The ankle module of claim 1, wherein the adapter portion comprises the three of more cylinders.

3. The ankle module of claim 1, wherein the ankle module has a longitudinal axis, the longitudinal axis extending parallel to a gap between a portion of a front surface of the base portion and a portion of a rear surface of the adapter portion when the ankle module is used by a person while standing in a neutral position.

4. The ankle module of claim 1, wherein the actuator comprises a spool valve selectively actuatable to allow or disallow fluid communication between the cylinders to adjust or fix the angular position of the adapter portion relative to the base portion.

5. The ankle module of claim 4, wherein the actuator comprises a push button that is coupled to the spool valve such that a person can selectively lock and unlock the angular position by pressing the push button.

6. The ankle module of claim 1, wherein the actuator is manually actuatable by a user.

7. The ankle module of claim 1, wherein the three or more cylinders are sized and spaced from the pivot connection so that a volume of hydraulic fluid that is displaced among the cylinders during adjustment of the angular position of the adapter portion is balanced among the cylinders.

8. The ankle module of claim 1, wherein the three or more cylinders are sized and spaced within the adapter portion from the pivot connection so that a volume of hydraulic fluid that is displaced between the cylinders during adjustment of the angular position of the adapter portion is unbalanced between the cylinders, the ankle module further comprising an accumulator that facilitates the pivoting of the adapter portion relative to the base portion.

9. The ankle module of claim 1, wherein the prosthetic ankle module has a longitudinal axis that is vertical when the ankle module is used by a person while standing.

10. A prosthetic foot comprising:
a plate-like foot member extending from a proximal portion to a distal portion, the foot member curving downward and forward toward the distal portion; and an ankle module removably coupleable to the proximal portion of the foot member, the ankle module comprising
a base portion coupleable to the proximal portion so that a surface of the base portion contacts a surface of the proximal portion, wherein the base portion comprises a central vertical axis and a length extending along the central vertical axis;
an adapter portion pivotally coupled to the base portion at a pivot connection located generally at a mid-point along the length of the ankle module and having a coupling member configured to removably couple the foot member to a prosthetic pylon or socket, one of the base and adapter portions having three or more cylinders formed therein, the three or more cylinders being aligned symmetrically relative to the pivot connection of the ankle module, the three or more cylinders housing corresponding pistons slidably displaceable within the cylinders, the cylinders selectively placeable in fluid communication with each other, wherein the adapter portion is pivotally coupled to the base portion about the pivot connection such that the adapter portion is allowed to pivot medial-laterally about a longitudinal axis, in a dorsi-plantar manner about a transverse axis, and about a normal axis relative to the base portion, and
an actuator selectively actuatable to place the three or more cylinders in fluid communication, allowing a hydraulic fluid to flow between the cylinders as an angular position of the adapter portion is adjusted relative to the base portion, the actuator selectively actuatable to fluidly isolate the cylinders from each other so that the angular position of the adapter portion relative to the base portion remains fixed, thereby adjusting the dorsi-plantar position between the adapter portion and the base portion of the ankle module.

11. The prosthetic foot of claim 10, wherein the adapter portion comprises the three or more cylinders.

12. The prosthetic foot of claim 10, wherein the ankle module has a longitudinal axis, the longitudinal axis extending parallel to a gap between a portion of a front surface of the base portion and a portion of a rear surface of the adapter portion when the ankle module is used by a person while standing in a neutral position.

13. The prosthetic foot of claim 10, wherein the proximal portion of the plate-like foot member extends vertically.

14. The prosthetic foot of claim 13, wherein the ankle module is configured to couple to the proximal portion of the foot member such that the adapter portion is positioned in front of a plane defined by the proximal portion of the foot member.

15. The prosthetic foot of claim 10, wherein the actuator comprises a spool valve selectively actuatable to allow or disallow fluid communication between the cylinders to adjust or fix the angular position of the adapter portion relative to the base portion.

16. The prosthetic foot of claim 15, wherein the actuator comprises a push button that is operatively coupled to the spool valve such that a person can selectively lock and unlock the angular position by pressing the push button.

17. The prosthetic foot of claim 10, wherein the actuator is manually actuatable by a user.

18. The prosthetic foot of claim 10, wherein the three or more cylinders are sized and spaced from the pivot connection so that a volume of hydraulic fluid that is displaced among the cylinders during adjustment of the angular position of the adapter portion is balanced among the cylinders.

19. The prosthetic foot of claim 10, wherein the three or more cylinders are sized and spaced within the adapter portion from the pivot connection so that a volume of hydraulic fluid that is displaced between the cylinders during adjustment of the angular position of the adapter portion is unbalanced between the cylinders, the ankle module further comprising an accumulator that facilitates the pivoting of the adapter portion relative to the base portion.

20. The prosthetic foot of claim 10, wherein the prosthetic ankle module has a longitudinal axis that is vertical when the ankle module is used by a person while standing.

* * * * *

UNITED STATES PATENT AND TRADEMARK OFFICE
CERTIFICATE OF CORRECTION

PATENT NO. : 9,687,365 B2  
APPLICATION NO. : 14/830102  
DATED : June 27, 2017  
INVENTOR(S) : Sigurdur Ásgeirsson Page 1 of 1

It is certified that error appears in the above-identified patent and that said Letters Patent is hereby corrected as shown below:

In the Specification

In Column 10 at Line 34, change "200"." to --200'".--.

Signed and Sealed this
Sixteenth Day of January, 2018

Joseph Matal
*Performing the Functions and Duties of the*
*Under Secretary of Commerce for Intellectual Property and*
*Director of the United States Patent and Trademark Office*